United States Patent
Simpson et al.

(12)

(10) Patent No.: US 6,616,657 B2
(45) Date of Patent: *Sep. 9, 2003

(54) RF ABLATION CATHETER TIP ELECTRODE WITH MULTIPLE THERMAL SENSORS

(75) Inventors: John A. Simpson, Carlsbad, CA (US); Wade A. Bowe, Temecula, CA (US); Thomas M. Castellano, Temecula, CA (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/948,334

(22) Filed: Sep. 6, 2001

(65) Prior Publication Data

US 2002/0022834 A1 Feb. 21, 2002

Related U.S. Application Data

(63) Continuation of application No. 09/515,382, filed on Feb. 29, 2000, now Pat. No. 6,312,425, which is a continuation-in-part of application No. 09/072,801, filed on May 5, 1998, now Pat. No. 6,042,580.

(51) Int. Cl.⁷ ............................................... A61B 18/18
(52) U.S. Cl. .......................................... 606/41; 607/102
(58) Field of Search ............................. 606/41, 45, 49, 606/50

(56) References Cited

U.S. PATENT DOCUMENTS

| 4,411,266 A | 11/1983 | Cosman |
| 5,277,201 A | 1/1984 | Stern |
| 4,966,597 A | 10/1990 | Cosman |
| 5,456,682 A | 10/1995 | Edwards et al. |
| 5,688,266 A | 11/1997 | Edwards et al. |
| 5,688,267 A | * 11/1997 | Panescu et al. ................ 606/41 |
| 5,713,942 A | 2/1998 | Stern et al. |
| 5,849,028 A | 12/1998 | Chen |
| 5,893,885 A | 4/1999 | Webster, Jr. |
| 5,935,124 A | 8/1999 | Klumb et al. |
| 6,270,493 B1 | * 4/2001 | Lalonde et al. ................ 606/23 |
| 6,312,425 B1 | * 11/2001 | Simpson et al. ............... 606/32 |
| 6,471,693 B1 | * 10/2002 | Carroll et al. ................. 606/21 |

FOREIGN PATENT DOCUMENTS

| WO | WO93/13816 | 7/1993 |
| WO | WO96/00036 | 1/1996 |
| WO | WO97/06739 | 2/1997 |
| WO | WO99/56645 | 11/1999 |
| WO | WO99/56647 | 11/1999 |

* cited by examiner

*Primary Examiner*—Roy D. Gibson
*Assistant Examiner*—Aaron Roane
(74) *Attorney, Agent, or Firm*—Fulwider Patton Lee & Utecht, LLP

(57) ABSTRACT

A tip electrode for an ablation catheter mounted at the distal tip of an elongated catheter body member has a distal-end region and a proximal-end region. A tip thermal sensor is located at or near the apex of the distal-end region and one or more side thermal sensors are located near the surface of the proximal-end region. The electrode is preferably an assembly formed from a hollow dome-shaped shell with a core disposed within the shell. The side thermal sensor wires are electrically connected inside the shell and the core has a longitudinal channel for the side thermal sensor wires welded to the shell. The shell also preferably has a pocket in the apex of the shell, and the end thermal sensor wires pass through the core to the apex of the shell. Spaces between the shell and the core can be filled with epoxy resin. Alternatively, the electrode is formed of a solid metal having a plurality of bores for positioning thermal sensors at the tip and near the surface of the electrode.

8 Claims, 6 Drawing Sheets

RF ABLATION CATHETER TIP ELECTRODE WITH MULTIPLE THERMAL SENSORS

RELATED APPLICATIONS

This application is a continuation of application Ser. No. 09/515,382 filed Feb. 29, 2000, now U.S. Pat. No. 6,312,425 which is a continuation-in-part of application Ser. No. 09/072,801 filed May 5, 1998, now U.S. Pat. No. 6,042,580, the disclosures of which are hereby incorporated by reference.

BACKGROUND OF THE INVENTION

1. Field of the Invention

The invention relates generally to electrophysiological ("EP") catheters for ablating tissue, and more particularly to an improved tip electrode for an ablation catheter having multiple thermal sensors for improved measurement of electrode/tissue interface temperature.

2. Description of the Related Art

The heart beat in a healthy human is controlled by the sinoatrial node ("S-A node") located in the wall of the right atrium. The S-A node generates electrical signal potentials that are transmitted through pathways of conductive heart tissue in the atrium to the atrioventricular node ("A-V node") which in turn transmits the electrical signals throughout the ventricle by means of the His and Purkinje conductive tissues. Improper growth of, or damage to, the conductive tissue in the heart can interfere with the passage of regular electrical signals from the S-A and A-V nodes. Electrical signal irregularities resulting from such interference can disturb the normal rhythm of the heart and cause an abnormal rhythmic condition referred to as "cardiac arrhythmia."

While there are different treatments for cardiac arrhythmia, including the application of anti-arrhythmia drugs, in many cases ablation of the damaged tissue can restore the correct operation of the heart. Such ablation can be performed by percutaneous ablation, a procedure in which a catheter is percutaneously introduced into the patient and directed through an artery to the atrium or ventricle of the heart to perform single or multiple diagnostic, therapeutic, and/or surgical procedures. In such case, an ablation procedure is used to destroy the tissue causing the arrhythmia in an attempt to remove the electrical signal irregularities and restore normal heart beat or at least an improved heart beat. Successful ablation of the conductive tissue at the arrhythmia initiation site usually terminates the arrhythmia or at least moderates the heart rhythm to acceptable levels. A widely accepted treatment for arrhythmia involves the application of RF energy to the aberrant conductive tissue.

In the case of atrial fibrillation ("AF"), a procedure published by Cox et al. and known as the "Maze procedure" involves continuous atrial incisions to prevent atrial reentry and to allow sinus impulses to activate the entire myocardium. While this procedure has been found to be successful, it involves an intensely invasive approach. It is more desirable to accomplish the same result as the Maze procedure by use of a less invasive approach, such as through the use of an appropriate EP catheter system.

There are two general methods of applying RF energy to cardiac tissue, unipolar and bipolar. In the unipolar method a large surface area electrode; e.g., a backplate, is placed on the chest, back or other external location of the patient to serve as a return. The backplate completes an electrical circuit with one or more electrodes that are introduced into the heart, usually via a catheter, and placed in intimate contact with the aberrant conductive tissue. In the bipolar method, two or more electrodes are introduced into the heart. The electrodes are oppositely charged and thus complete an electrical circuit between themselves. In the bipolar method, the flux traveling between the two electrodes of the catheter enters the tissue to cause ablation.

During ablation, the electrodes are placed in intimate contact with the target endocardial tissue. RF energy is applied to the electrodes to increase the temperature of the target tissue to a non-viable state. In general, the temperature boundary between viable and non-viable tissue is approximately 48° Centigrade. Tissue heated to a temperature above 48° C. becomes non-viable and defines the ablation volume. For therapeutic effectiveness, the ablation volume must extend a few millimeters into the endocardium and must have a surface cross-section of at least a few millimeters square. The objective is to elevate the tissue temperature, which is generally at 37° C., fairly uniformly to an ablation temperature above 48° C., while keeping both the temperature at the tissue surface and the temperature of the electrode below 100° C.

During ablation, portions of the electrodes are typically in contact with the blood, so that it is possible for clotting and boiling of blood to occur if those electrodes reach an excessive temperature. Both of these conditions are undesirable. Clotting is particularly troublesome at the surface of the catheter electrode because the impedance at the electrode rises to a level where the power delivery is insufficient to effect ablation. Additionally, too great a rise in impedance can result in tissue dessication and/or tissue explosion and thrombus formation within the heart, both of which are also undesirable. When any of these conditions arise, the ablation procedure must be stopped and the catheter removed and cleaned or replaced before the procedure can continue. Such delay in an ablation procedure is undesirable in that it may prove critical to the patient's heath or survival.

Even though no significant amount of heat is generated in the electrodes themselves, adjacent heated endocardial tissue heats the electrodes via heat conduction through the tissue. As mentioned above, part of the active electrode will be in contact with the blood in the heart and if the electrode temperature exceeds 90–100° C., it can result in blood clotting on the electrode. The application of RF energy must then be stopped. However, shutting the RF generator off due to the temperature rise may not allow sufficient time to complete the entire ablation procedure. Providing an ablation electrode capable of applying higher amounts of power for a longer period of time to ablate the damaged tissue to an acceptable depth is a goal of current ablation catheter electrode design. It has been found that higher power for longer time periods results in a higher probability of success of the ablation procedure.

To avoid clotting and blood boiling, RF ablation catheters for cardiac applications typically provide temperature feedback during ablation via a temperature sensor such as a thermocouple. In its simplest form, a thermocouple consists of two dissimilar metals joined together at one end called a "bead" or junction, such as a conventional copper/constantan type "T" thermocouple. When the junction is heated a thermoelectric potential arises and can be measured across the unconnected ends. This is also known as the thermoelectric or Seebeck effect. This voltage is proportional to the temperature difference between the junction and the non-joined ends.

Many RF ablation catheters include a tip electrode for "end-fire" ablation. The catheter is oriented such that the end of the tip electrode is in contact with the target tissue and RF energy is then applied. A tip electrode may contain a single end thermal sensor, typically located along the centerline of the tip, at or very near the apex of the tip electrode. The temperature sensor is thus in close proximity to the electrode/tissue interface when the tip electrode is oriented such that the apex of the electrode contacts the tissue during ablation, i.e. the "end-fire" mode. If, however, the side of the tip contacts the tissue during ablation, i.e. the "side-fire" mode, the radial distance from the end thermal sensor to the electrode/tissue interface is roughly equal to half the diameter of the tip electrode (e.g., approximately 1.167 mm for a 7 French diameter tip). There can therefore be a significant difference in the temperature measurements provided by the end thermal sensor depending on the orientation of the tip electrode.

During ablation, the temperature measured by a conventional ablation electrode positioned in the end-fire mode is closer to the actual tissue-interface temperature than the temperature measured when the electrode is positioned in the side-fire mode. The difference in measured temperature from actual tissue-interface temperature in the side-fire mode measurements is increased by high blood flow in the vicinity of the electrode. The high blood flow causes a steeper thermal gradient to arise within the tip electrode due to the increase in cooling of the electrode that the flow provides. This effect is commonly referred to as "back-side cooling."

It is most advantageous for the thermal sensor to be located as close as possible to the electrode/tissue interface. However, in conventional catheters having a tip electrode containing only a single thermal sensor located at the end, a performance compromise between the side-fire and end-fire modes is commonly made in the design of the catheter. Additionally, tip electrodes provide other considerations in mounting temperature sensors. A tip electrode must be well anchored to the catheter shaft so that separation does not occur. Additionally, it must be thick enough to draw heat away from the tissue interface for cooling purposes yet not too thick so as to unduly increase the outside diameter of the catheter. Attaching a power lead to the tip electrode so that RF energy may be conducted by the electrode already adds one lead to the pair of leads connected to the sensor located at the end of the electrode.

Hence those skilled in the art have identified a need for improvement of overall temperature measurement in the tip electrode of an ablation catheter that can be used for both end-fire and side-fire ablation. Improved measurement capability can result in increased product efficacy, because the potential for a rise in electrical impedance, which typically prevents further delivery of RF energy, is reduced. The likelihood of thrombus formation is also reduced. It is also desirable to provide for an improved temperature feedback control system in an ablation energy delivery system configured as a closed loop system, with power being adjusted to maintain the temperature of the electrode/tissue interface below a threshold temperature. The present invention fulfills these needs and others.

SUMMARY OF THE INVENTION

Briefly, and in general terms, the present invention is directed to a tip electrode for use within an ablation catheter, with improved electrode/tissue interface temperature measurement capability for both end-fire and side-fire ablation modes.

In a first aspect, the invention relates to a tip electrode adapted to be mounted to a catheter for providing electrical energy to biological tissue. The tip electrode includes a distal-end portion, a proximal-end portion contiguous with the distal-end portion, at least one distal-end thermal sensor electrically connected to the distal-end portion, and at least one proximal-end thermal sensor electrically connected to the proximal-end portion.

In detailed aspects, the distal-end portion is substantially dome-shaped and the at least one distal-end thermal sensor is connected near the apex of the dome and the proximal-end portion is substantially cylindrical shaped and the proximal-end thermal sensor is connected near the surface of the proximal-end portion. In a more detailed facet, the tip electrode includes a plurality of proximal-end thermal sensors connected at distinct points around a circumference of the proximal-end portion. In another detailed facet, the distal-end portion and the proximal-end portion are formed of a first metallic material and the at least one distal-end thermal sensor includes a first electrical lead connected to the distal-end portion, the first lead formed of a second metallic material different than the first metallic material and having a Seebeck coefficient relative the first metallic material and a second electrical lead connected to the tip electrode, the second lead formed of a third metallic material and having a Seebeck coefficient relative the first metallic material. The ratio of the magnitude of the Seebeck coefficient of the second metallic material relative to the first metallic material and the magnitude of the Seebeck coefficient of the third metallic material relative to the first metallic material is at least ten to one.

In yet another detailed aspect, the distal-end portion and the proximal-end portion are formed of a first metallic material and the at least one proximal-end thermal sensor includes a first electrical lead connected to the distal-end portion, the first lead formed of a second metallic material different than the first metallic material and having a Seebeck coefficient relative the first metallic material and a second electrical lead connected to the tip electrode, the second lead formed of a third metallic material and having a Seebeck coefficient relative the first metallic material. The ratio of the magnitude of the Seebeck coefficient of the second metallic material relative to the first metallic material and the magnitude of the Seebeck coefficient of the third metallic material relative to the first metallic material is at least ten to one.

In a second facet, the invention is related to a tip electrode adapted to be mounted at the distal-end of an elongated catheter for ablating biological tissue. The biological tissue is located in a biological structure in which fluids flow past the tissue to be ablated. The electrode includes a dome-shaped distal-end portion, a cylindrical shaped proximal-end portion contiguous with the distal-end portion, a tip thermal sensor electrically connected to the distal-end portion and at least one peripheral thermal sensor electrically connected near the surface of the proximal-end portion.

In a detailed aspect, the distal-end portion includes a pocket near the apex of the distal-end portion and the first thermal sensor is positioned in the pocket. In another detailed facet, the distal-end portion is solid and carries a tip-sensor bore terminating in a pocket near the apex of the distal-end portion and the tip thermal sensor is positioned in the pocket. In yet another detailed aspect, the proximal-end portion comprises a hollow tube and the at least one peripheral thermal sensor is positioned at the inside surface of the tube. In still another detailed aspect, the tip electrode further includes a hollow core positioned within the hollow tube for feeding through the tip sensor to the distal-end portion. In yet another detailed facet, the proximal-end portion is solid and carries at least one peripheral-sensor bore and the at least one peripheral thermal sensor is positioned in the bore.

In a third facet, the invention relates to an apparatus for delivering energy to biological tissue. The apparatus includes a catheter having a tip electrode formed of a first metallic material. The tip electrode is disposed at a distal end of the catheter and the distal end is adapted to be positioned so that the tip electrode is located proximal the biological tissue. The apparatus further includes a plurality of electrically conductive sensor leads, each individually electrically connected to the tip electrode. One senor lead is electrically connected near the apex of the tip electrode to form an apex sensor junction while each of the remaining sensor leads are electrically connected proximal the apex to form a peripheral sensor junction. Each sensor junction has a temperature-dependent voltage associated therewith. The apparatus further includes an electrically conductive common lead electrically connected to the tip electrode to form a common junction. The common lead is formed of a second metallic material such that substantially no temperature-dependent voltage is associated with the common junction.

In a detailed facet, each of the sensor leads is formed of a metallic material different than the first metallic material and each metallic material has a known Seebeck coefficient relative to the first metallic material. In another detailed aspect, the ratio of the magnitude of the Seebeck coefficient of the sensor lead metallic material relative to the first metallic material and the magnitude of the Seebeck coefficient of the common lead metallic material relative to the first metallic material is at least ten to one. In another detailed aspect, there are four peripheral sensor junctions and the peripheral sensor junctions are connected to the tip electrode approximately 90° apart around a circumference of the tip electrode.

These and other aspects and advantages of the invention will become apparent from the following detailed description and the accompanying drawings, which illustrate by way of example the features of the invention.

BRIEF DESCRIPTION OF THE DRAWINGS

FIG. 6a is a longitudinal view of the core of the tip electrode of FIG. 5a;

FIG. 6b is an end view of the core of the tip electrode shown in FIG. 6a taken along line 6b—6b;

FIG. 7a is a longitudinal view of the shell of the tip electrode of FIG. 5a;

FIG. 7b is an end view of the shell of the tip electrode taken along line 7b—7b;

FIG. 9a is a longitudinal view of the core of the tip electrode of FIG. 8a;

FIG. 10a is a cross-sectional view of the shell of the tip electrode of FIG. 8a;

FIG. 12a is a longitudinal view of the core of the tip electrode of FIG. 12a;

DETAILED DESCRIPTION OF THE PREFERRED EMBODIMENTS

Figure 1:
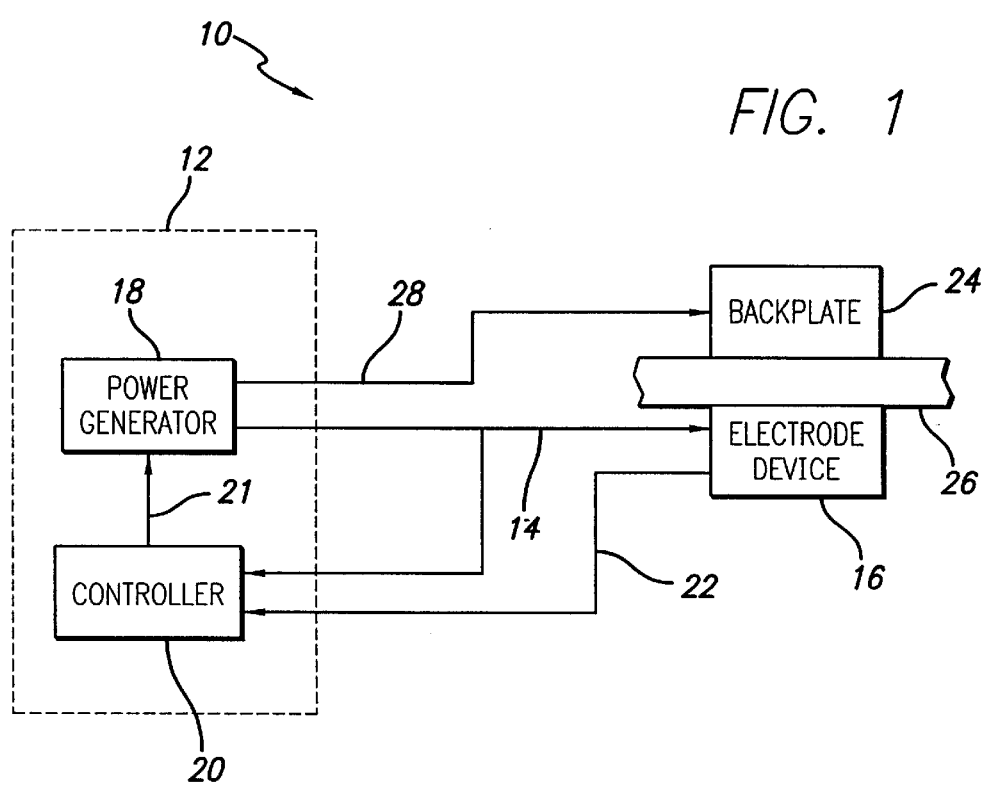
FIG. 1 is a schematic diagram of an ablation apparatus including a power generator, controller, backplate, and an electrode device.

Turning now to the drawings, in which like reference numerals are used to designate like or corresponding elements among the several figures, in FIG. 1 there is shown an ablation apparatus 10 in accordance with aspects of the present invention. The apparatus 10 includes a power control system 12 that provides power or drive signals 14 to an electrode device 16. The power control system 12 comprises a power generator 18 that may have any number of output channels through which it provides the power signals 14. The operation of the power generator 18 is controlled by a controller 20 which outputs control signals 21 to the power generator 18. The controller 20 monitors the power signals 14 provided by the power generator 18. In addition, the controller 20 also receives temperature signals 22 from the electrode device 16. Based on these power signals 14 and temperature signals 22 the controller 20 adjusts the operation of the power generator 18. A backplate 24 is located proximal to the biological site 26 opposite the site from the electrode device 16, and is connected by a backplane wire 28 to the power generator 18. The backplate 24 is set at the reference level to the power signals provided to the electrodes, as discussed in detail below.

Figure 2:
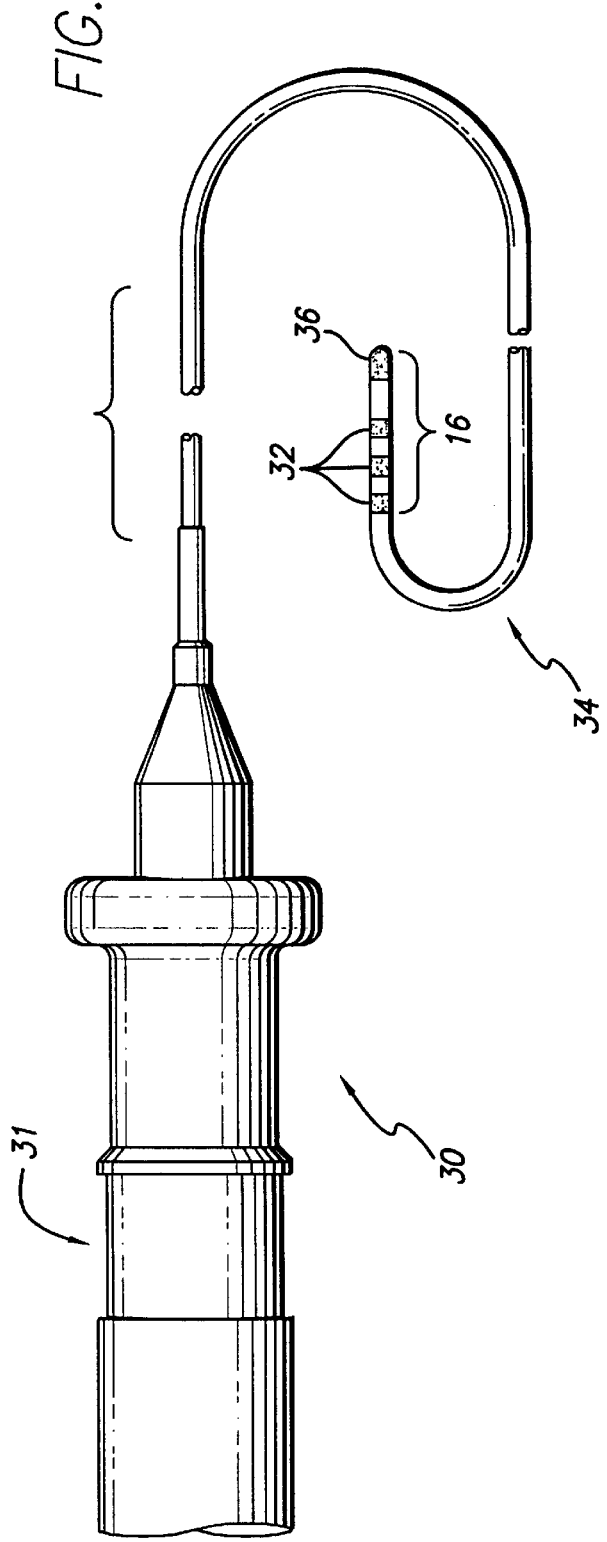
FIG. 2 is a diagram of a catheter system including a handle, steering member and a catheter carrying an electrode device having a tip electrode in accordance with aspects of the invention.

As shown in FIG. 2, the electrode device 16 is typically part of a steerable EP catheter 30 capable of being percutaneously introduced into a biological site 26, e.g., the atrium or ventricle of the heart. In this embodiment, the catheter 30 comprises a distal segment 34 and a handle 31 located outside the patient. A preferred embodiment of the electrode device 16 includes three band electrodes 32 and a tip electrode 36 arranged in a substantially linear array along the distal segment 34 of the catheter 30. The band electrodes 32 and tip electode 36 are used for the collection of intracardiac electrograms. The tip electrode 36 is also used to deliver RF energy to the biological site 26 to form spot lesions.

The tip electrode 36 is designed to heat a volume of tissue to an ablation temperature while at the same time assuring that the peak temperature of the tip electrode is controlled so that clotting does not foul the electrode surface and blood boiling does not occur. To this end, the tip electrode 36 is formed from a biocompatible material having a high thermal conductivity. The following metals are provided for example in descending order of electrical conductivity as measured using the International Annealed Copper Standard (IACS): silver, gold, chromium, aluminum, molybdenum, tungsten, nickel, platinum, and platinum/10% iridium.

In one embodiment, that material is substantially pure platinum. Pure platinum is preferred over platinum/10% iridium, which is commonly used in electrophysiology catheters, because it has been found to produce larger lesions with lesser incidence of impedance rise at the electrode/tissue interface. Pure platinum also has a more reliable thermoelectric performance. To further assure that the peak temperature of the tip electrode 36 is controlled, it is sized and shaped so that a large surface area is available for contact with the fluid in the heart for dissipating heat to the fluid around the electrode and thereby cooling the electrode. In a preferred embodiment, the active tip electrode is 7 French and 5 mm long. In other embodiments the active tip electrode may be up to 10 mm long. These longer tip electrodes tend to produce substantially larger lesion volumes than the 5 mm long tip electrode.

Figure 3:
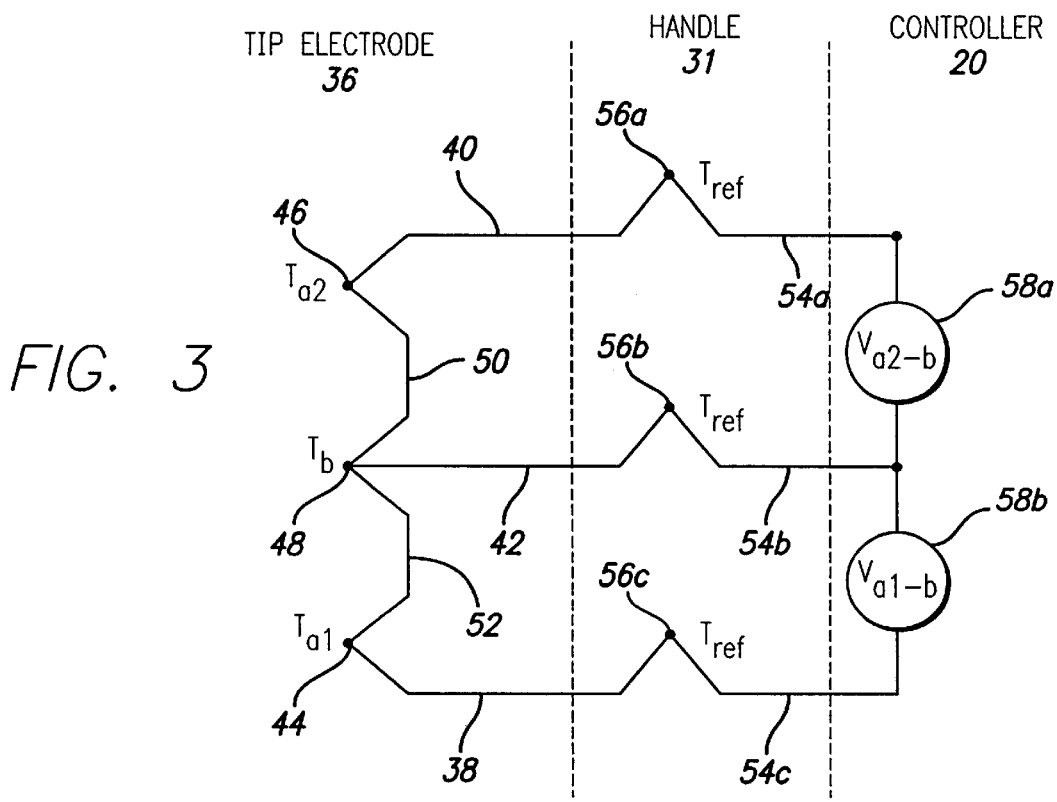
FIG. 3 is a schematic diagram of a thermocouple system having two sensor thermocouple wires and a composition-matched, common-lead thermocouple wire attached to a wire simulating a portion of a tip electrode.
Figure 4:
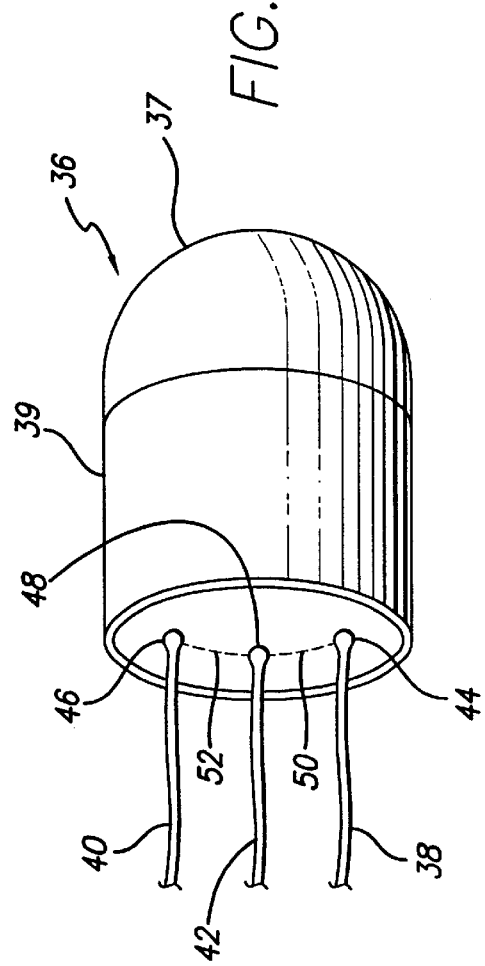
FIG. 4 is a diagram of a tip electrode showing the connection of two sensor thermocouple wires and a composition-matched, common-lead thermocouple wire.
Figures 5A, 5B:
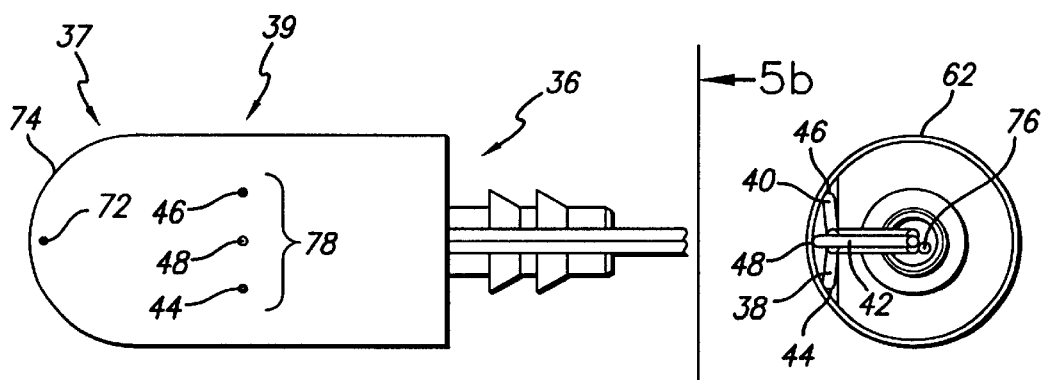
FIG. 5a is a longitudinal view of one embodiment of the tip electrode of FIG. 2 having a shell and core and showing the location of a tip sensor and multiple side sensors.
FIG. 5b is an end view of the tip electrode shown in FIG. 5a taken along the line 5b—5b of FIG. 5a and showing the location of and attachment of sensor leads to the electrode.
Figures 6A, 6B:
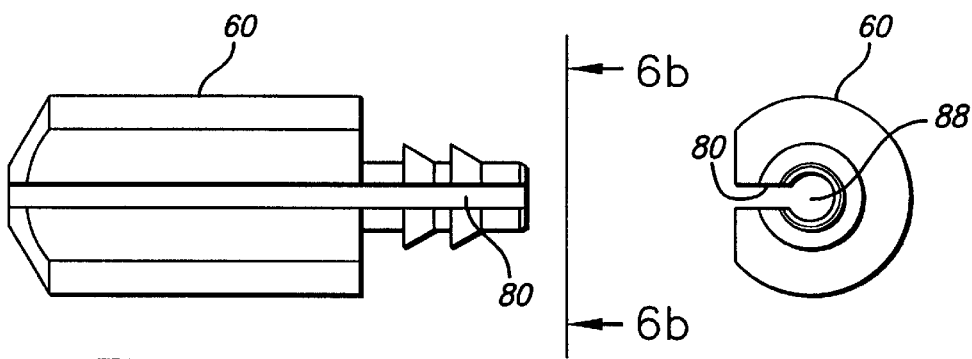
Figures 7A, 7B:
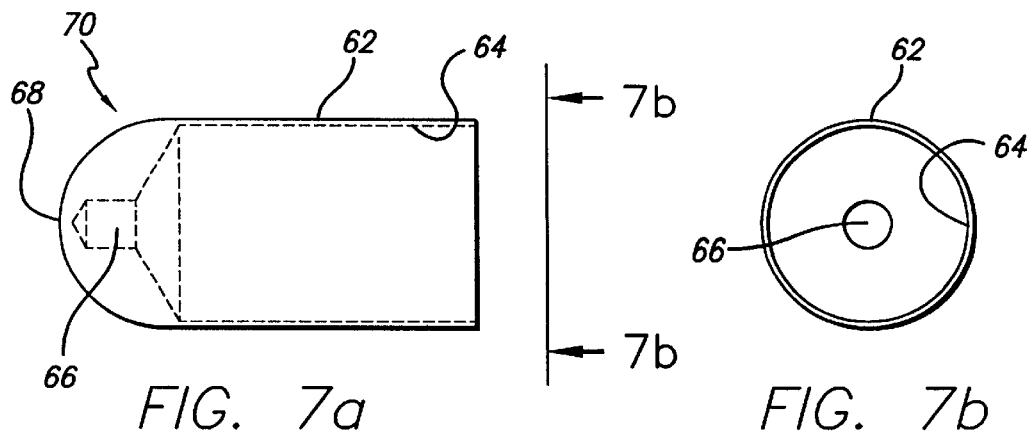
Figure 8A:
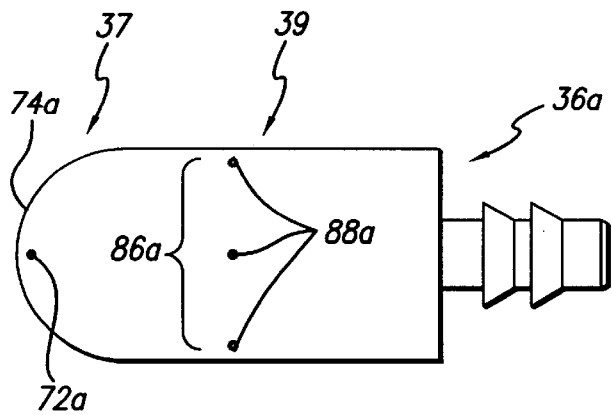
FIG. 8a is a longitudinal view of another embodiment of the tip electrode of FIG. 2 having a shell and core and showing the location of a tip sensor and multiple side sensors.
Figure 8B:
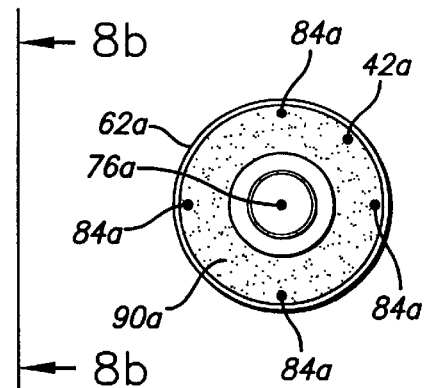
FIG. 8b is an end view of the tip electrode shown in FIG. 8a taken along the line 8b—8b of FIG. 8a and showing the location of and attachment of sensor leads to the electrode.
Figure 9A:
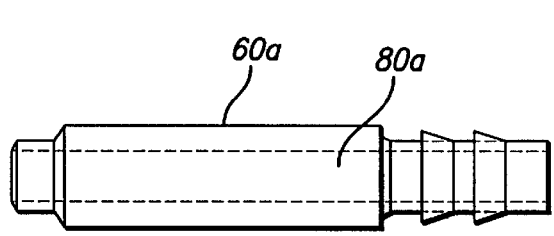
Figure 9B:
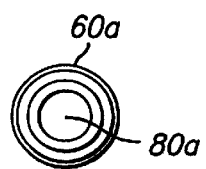
FIG. 9b is an end view of the core of the tip electrode shown in FIG. 9a taken along line 9b—9b.
Figure 10A:
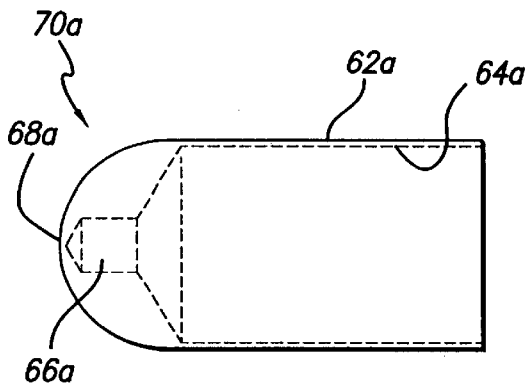
Figure 10B:
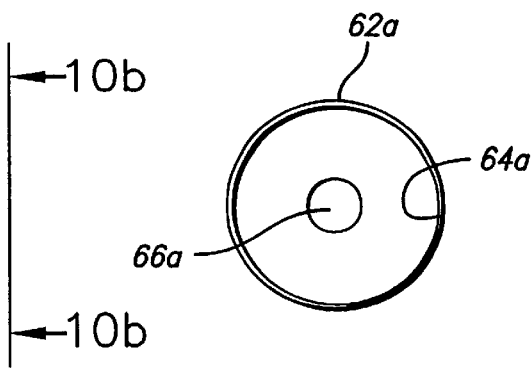
FIG. 10b is an end view of the shell of the tip electrode of FIG. 10a taken along line 10b—10b.
Figure 11A:
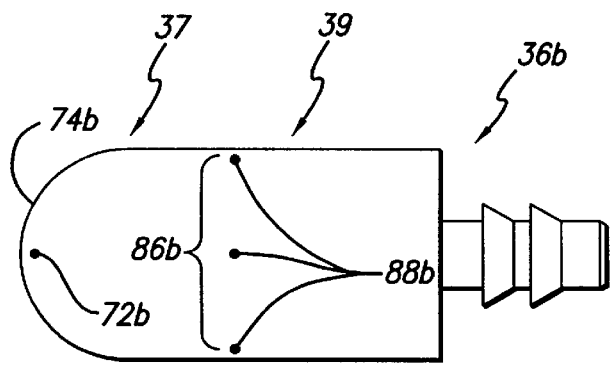
FIG. 11a is a longitudinal view of one embodiment of the tip electrode of FIG. 2 having a solid core and showing the location of a tip sensor and multiple side sensors.
Figure 11B:
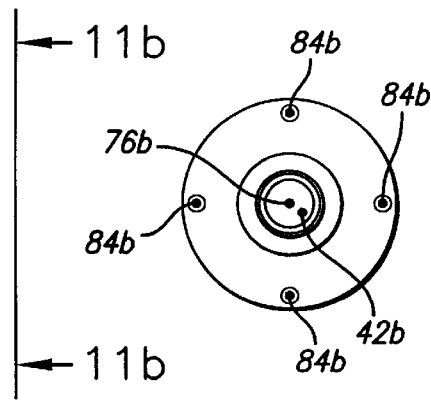
FIG. 11b is an end view of the tip electrode shown in FIG. 11a taken along the line 11b—11b of FIG. 11a and showing the location of and attachment of sensor leads to the electrode.
Figure 12A:
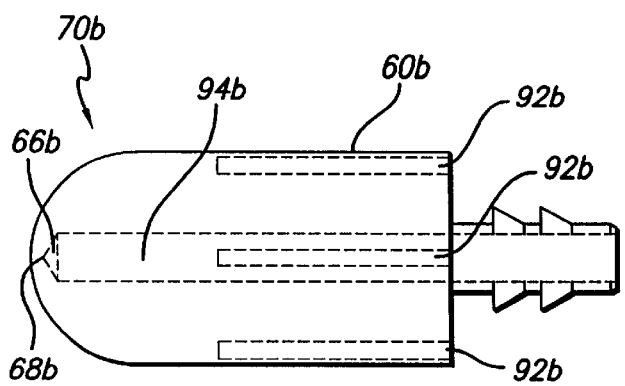
Figure 12B:
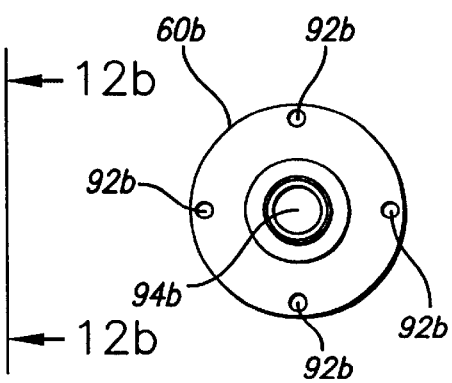
FIG. 12b is an end view of the core of the tip electrode shown in FIG. 12a taken along line 12b—12b.

In accordance with aspects of the present invention, and with reference to FIGS. 3 and 4, the tip electrode 36 includes a substantially dome-shaped distal-end portion 37 and a substantially cylindrical proximal-end portion 39. The two portions 37, 39 of the electrode 36 are contiguous and are preferably formed as a single unitary structure, as described in detail below with reference to various embodiments of the tip electrode 36.

A first electrically conductive sensor lead 38, second electrically conductive sensor lead 40, and electrically conductive common lead 42 are connected independently to the inside of the proximal-end portion 39 at two sensor junctions 44 and 46, and a common junction 48 respectively. Each of these junctions 44, 46, 48 are separate from each other and are preferably located around a circumference of the proximal-end portion 39. As described in detail below, these three electrically conductive members 38, 42, and 40 form the leads, i.e., or "legs" of what is essentially two thermocouples. Because of the separation between the locations at which the leads are attached to the inside surface of the tip electrode, the portions 50 and 52 of the tip electrode 36 between the connection points 44, 48, and 46 become part of the thermocouples and, in effect, serve as a large thermocouple bead. Associated with two of the junctions 44, 46 is a temperature-dependent voltage. This voltage is produced by the interface between two dissimilar metals, e.g., a platinum tip electrode and a constantan lead, and fluctuates in accordance with the temperature of the junction.

A conductive lead 54a, 54b, 54c is electrically connected to each sensor lead 38, 40 and the common lead 42 at a reference junction 56a, 56b, 56c. A voltmeter 58b is disposed across the conductive lead 54c connected to the first sensor lead 38 and the conductive lead 54b connected to the common lead 42 to measure the temperature-dependent voltage developed in the thermocouple formed by sensor lead 38, common lead 42, and thermocouple bead 52. Similarly, a voltmeter 58a is disposed across the conductive lead 54a connected to second sensor lead 40 and the conductive lead 54b connected to the common lead 42 to measure the temperature-dependent voltage developed in the thermocouple formed by sensor lead 40, common lead 42, and thermocouple bead 50. The reference junctions 56a, 56b, 56c and the leads 54a, 54b, 54c for use in connection to the voltmeters 58a, 58b are located in the handle 31 of the catheter and are therefore outside the patient. In another embodiment, the reference junctions 56a, 56b, 56c and conductive leads 54a, 54b, 54c are omitted and, as explained below, the reference temperature is assumed to be room temperature.

While FIGS. 3 and 4 depict only two sensor leads 38 and 40 it is possible to include a larger number of sensor leads. In some embodiments of the invention, a sensor lead is positioned at the apex of the distal-end portion 37 with additional sensor leads positioned at distinct points around a circumference of the proximal-end portion 39. With continued reference to FIGS. 3 and 4, each such sensor lead forms, in combination with the single common lead 42 and the thermocouple bead formed by the portion of the tip electrode 36 between the sensor lead and common lead, a separate thermocouple. Each of these thermocouples provides a temperature-dependent voltage indicative of the temperature at the junction where the sensor lead is connected to the tip electrode 36.

Conductive leads 38, 40, 54a, 54c are connected to voltmeters 58a, 58b located within the controller 20 (FIG. 1). A common lead 42, 54b is also connected to the voltmeters 58a, 58b. The voltmeters 58a, 58b (FIG. 3) provide voltage readings which are related to the temperatures at the various junctions 44, 46, 48, 56a, 56b, 56c. The resulting voltage output $V_{a1-b}$ measured by one of the voltmeters 58b is expressed by the following general equation:

$$V_{a1-b} = \alpha_{ac}(T_{a1} - T_{ref}) - \alpha_{bc}(T_b - T_{ref}) \quad \text{(Eq. 5a)}$$

where:

$\alpha_{ac}$=Seebeck coefficient for the first sensor lead 38 material and the band material $\alpha_{bc}$=Seebeck coefficient for the common lead 42 material and the band material $T_{a1}$=temperature at the first sensor lead/electrode junction 44

$T_b$=temperature at the common lead/electrode junction 48

$T_{ref}$=temperature at the first sensor lead 38 reference junction 56c and at the common lead 42 reference junction 56b The reference temperature $T_{ref}$ and the two Seebeck coefficients, $\alpha_{ac}$ and $\alpha_{bc}$, are typically known for the system at hand.

The resulting voltage output $V_{a2-b}$ measured by the other voltmeter 58a is expressed by the following general equation:

$$V_{a2-b} = \alpha_{ac}(T_{a2} - T_{ref}) - \alpha_{bc}(T_b - T_{ref}) \quad \text{(Eq. 5b)}$$

where:

$\alpha_{bc}$ and $T_b$ are the same as described with reference to Eq. 5a $\alpha_{ac}$ = Seebeck coefficient for the second sensor lead 40 material and the band material $T_{a2}$ = temperature at the second sensor lead/electrode junction 46

$T_{ref}$ = temperature at the second sensor lead 40 reference junction 56a and temperature at the common lead 42 reference junction 56b Again, the reference temperature $T_{ref}$ and the two Seebeck coefficients, $\alpha_{ac}$ and $\alpha_{bc}$, are typically known for the system at hand.

As mentioned briefly above, the reference junctions 56a, 56b, 56c are controlled temperature junctions which are normally included in order to correct for extraneous voltages due to dissimilar metal junctions at the voltmeter terminals. By being located in the handle, for example, the temperatures at these references are known to be room temperature, or approximately 22° C.(72° F.). In addition, the Seebeck coefficients are assumed to be constant over the range of temperatures typically encountered in cardiac ablation.

In accordance with the present invention, the material of the common lead 42 is chosen such that the temperature-dependent voltage produced at the common junction 48 is substantially zero. This is preferably done by forming the common lead 42 of the same material as the tip electrode 36 or alternatively by forming the common lead of a material having a thermoelectric output very similar to that of the band-electrode material. Thus the tip electrode 36 is described as having a "composition-matched" common lead 42. In one embodiment of the invention the tip electrode 36 and the common lead 42 are formed of substantially pure platinum. In another embodiment, the tip electrode 36 is formed of substantially pure platinum and the common lead is formed of a copper/nickel alloy containing approximately 1–2% nickel, which is known to those skilled in the art as "alloy-11." In addition to its platinum like thermoelectric properties, alloy-11 is also preferred because it is a low cost alternative to pure platinum leads. In either embodiment, $\alpha_{bc}$ approximately equals zero and Eq. 5a and 5b reduce to:

$$V_{a1-b} = \alpha_{ac}(T_{a1} - T_{ref}) \quad \text{(Eq. 6a)}$$

$$V_{a2-b} = \alpha_{ac}(T_{a2} - T_{ref}) \quad \text{(Eq. 6b)}$$

The materials of the first and second sensor leads 38, 40 are chosen such that the magnitude of the Seebeck coefficients of the materials relative to the tip electrode 36 material is large. In order to increase the voltage output and improve temperature measurement resolution, preferably, the material of the first and second sensor leads 38, 40 is chosen such that the ratio of the magnitude of the Seebeck coefficient of the sensor lead 38, 40 material relative to the tip electrode 36 material and the magnitude of the Seebeck coefficient of the common lead 42 material relative to the tip electrode 36 is at least ten to one. In one preferred embodiment, the first and second sensor leads 38 and 40 are formed of constantan. Constantan is preferred because it has a large Seebeck coefficient relative to platinum and it is a commercially available alloy produced to tight thermoelectric property tolerances. These legs 38, 40 are connected to a tip electrode 36 formed of substantially pure platinum. For pure platinum tip electrode 36, the following table provides approximate Seebeck coefficients (averaged over the temperature range of from zero to 100° C.) for a variety of different metals and alloys.

| METAL OR ALLOY | SEEBECK COEFFICIENT (mV/C) vs. PURE PLATINUM |
|---|---|
| Bismuth | −0.0734 |
| Constantan | −0.0351 |
| Nickel | −0.0148 |
| Cobalt | −0.0133 |
| Alumel | −0.0129 |
| Mercury | −0.0060 |
| Palladium | −0.0057 |
| Calcium | −0.0051 |
| Gold-chromium | −0.0017 |
| Thorium | −0.0013 |
| Platinum | 0 |
| Alloy-11 | +0.0013 |
| Tantalum | +0.0033 |
| Aluminum | +0.0042 |
| Tin | +0.0042 |
| Lead | +0.0044 |
| Magnesium | +0.0044 |
| Stainless steel, 18–8 | +0.0044 |
| Solder 96.5Sn/3.5Ag | +0.0045 |
| Solder 50Sn/50Pb | +0.0046 |
| Phosphor bronze | +0.0055 |
| Thallium | +0.0058 |
| Yellow brass | +0.0060 |
| Manganin | +0.0061 |
| Iridium | +0.0065 |
| Copper-beryllium | +0.0067 |
| Indium | +0.0069 |
| Rhodium | +0.0070 |
| Silver | +0.0074 |
| Copper | +0.0076 |
| Zinc | +0.0076 |
| Gold | +0.0078 |
| 60Ni/24Fe/16Cr | +0.0085 |
| Cadmium | +0.0090 |
| Tungsten | +0.0112 |
| Cerium | +0.0114 |
| 80Ni/20Cr | +0.0114 |
| Spring steel | +0.0132 |
| Molybdenum | +0.0145 |
| Lithium | +0.0182 |
| Iron | +0.0189 |
| Chromel P | +0.0281 |
| Antimony | +0.0489 |

Thus in accordance with the present invention, the arrangement shown in FIGS. 3 and 4 provides for multiple temperature-sensitive locations, i.e., junctions 44, 46, on the tip electrode 36 using only three thermocouple wires 38, 42, 40, as opposed to two thermocouple pairs, i.e., four wires, thus resulting in a considerable saving of space in the ablation catheter.

In FIG. 4, a tip electrode 36 is shown having a composition-matched common lead 42 and two sensor leads 38, 40 at the inside surface of the band. Each lead 38, 42 and 40 is separately connected to the tip electrode 36 to form the three junctions 44, 48, and 46. Though the two sensor leads 38, 40 may be located anywhere on the tip electrode 36 they are preferably positioned approximately 60° apart around the circumference of the tip electrode. The common lead 42 maybe positioned anywhere on the tip electrode 36. In one embodiment (not shown) a separate power lead conducts power to the tip electrode 36 to impart ablation energy to the biological target tissue. Thus, four leads are used to provide power and to provide temperature sensing in two locations as opposed to five leads which would be required if each thermocouple had two leads.

In a preferred embodiment, the common lead 42 is also used to conduct power to the tip electrode 36 to impart ablation energy to the biological target tissue. Thus, in the preferred embodiment only three leads 38, 42, 40 are used to provide power and to sense in two locations at the tip electrode 36 rather than five leads as required by an electrode employing conventional thermocouples. This can result in a substantial savings in size because of the existence of fewer leads to be housed by the catheter.

With reference to FIGS. 5a through 7b, a tip electrode 36 in accordance with aspects of the present invention is shown and is adapted to be mounted at the distal end 34 of the electrode device 16. The tip electrode 36 (FIGS. 5a and 5b) is formed as an assembly of a core or post 60 illustrated in FIGS. 6a and 6b, and a hollow dome-shaped shell or cap 62 illustrated in FIGS. 7a and 7b, having an inner chamber 64 dimensioned to receive the core 60. In a preferred embodiment, both the core 60 and shell are formed of platinum. During assembly, the cap 62 is welded to the post 60. When assembled, the cap 62 and post 60 combine to define the distal-end portion 37 and the proximal-end portion 39 of the tip electrode 36.

A side thermal sensor system 78 having two sensor junctions 44, 46 is also preferably disposed at the side surface of the tip electrode 36. In one preferred embodiment, the side thermal sensor system 78 is formed by a common wire or "leg" 42 and two side sensor leads 38 and 40 as previously described with reference to FIG. 4. To provide clearance for the side thermal sensor leads 38, 40 the core has a longitudinal channel 80 allowing the side thermal sensor wires to be routed from the side thermal sensors system 78 to the main lumen (not shown) of the catheter. The common leg is preferably formed of alloy-11, and the two side sensor leads are formed of constantan. The side thermal sensor leads 38, 40 are typically welded inside the hollow dome-shaped shell 62. The junctions at which the thermal sensor lead 38, 40 and the shell 62 electrically connect form the sensor junctions 44, 46.

The shell 62 has a pocket 66 formed approximately in the apex 68 of the domed end 70 of the shell 62. The pocket 66 provides space for mounting a tip-sensor lead 76 at or adjacent the distal end 74 of the electrode along the center line. The tip-sensor lead 76 is typically formed of the same material as the first and second sensor leads 38, 40. The tip-sensor lead 76 in combination with the common lead 42 forms a tip-sensor junction 72 located at or near the apex of the distal end 74 of the active tip electrode 36. This ensures that the tip-sensor junction 72 is located at or near the electrode/tissue interface when the electrode is oriented in the end-fire mode. The tip-sensor lead 76 is also fed through a central aperture 88 through the core 60 and is preferably soldered into the pocket 66 within the apex 68. Epoxy resin is typically used to fill the voids between the shell 62 and the core 60. By placing the thermal sensor system 78 at the side surface of the tip electrode 36 the chances that one of the side sensor junctions 44, 46 is located at or near the electrode/tissue interface when the electrode is oriented in the side-fire mode are increased.

In another configuration, with reference to FIGS. 8a through 10b, a tip electrode 36a in accordance with aspects of the present invention is shown and is adapted to be mounted at the distal end 34 of the electrode device 16. The tip electrode 36a (FIGS. 8a and 8b) is formed as an assembly of a core or post 60a illustrated in FIGS. 9a and 9b, and a hollow dome-shaped shell or cap 62a illustrated in FIGS. 10a and 10b, having an inner chamber 64a dimensioned to receive the core 60a. In a preferred embodiment, the core 60a is formed of a material having low heat transfer properties, such as stainless steel or plastic. Experimentation has shown that the use of such material reduces heat transfer within the tip electrode 36 and between the temperature sensors located within the electrode. Thus, the heat present at one temperature sensor does not significantly effect the heat at the other temperature sensors and more reliable readings of the temperatures at the electrode/tissue interfaces are obtained. The core 60a in this configuration has a smaller diameter than the core 60 of the previously described configuration depicted in FIGS. 5a through 7b. As explained below, the small size of the core further assists in reducing the heat transfer within the tip electrode 36. In a preferred embodiment, the shell 62a is formed of platinum. During assembly, the post 60a is press fit into the cap 62a. When assembled, the cap 62a and post 60a combine to define the distal-end portion 37 and the proximal-end portion 39 of the tip electrode 36.

The shell 62a also preferably has a pocket 66a formed approximately in the apex 68a of the domed end 70a of the shell 62a. The pocket 66a provides space for mounting a tip-sensor lead 76a at or adjacent the distal end 74a of the electrode along the center line. To provide clearance for the tip-sensor lead 76a the core 60a has a longitudinal channel 80a allowing the tip-sensor lead to be routed from the tip-sensor junction 72a to the main lumen (not shown) of the catheter. The tip-sensor lead 76a is soldered within the pocket 66a, at or near the apex 68a.

The cap 62a also provides an inside surface for mounting a plurality of peripheral sensor leads 84a and a common lead 42a for electrical communication with the cap. The peripheral sensor leads 84a are preferably welded at distinct points around a circumference of the tubular portion of the cap 62a. In a preferred embodiment there are four peripheral sensors mounted 90° apart around the circumference of the cap 62a. Greater or fewer peripheral leads 84a may be mounted, depending on the size of the cap 62a and the lead capacity of the catheter lumen. The common lead 42a may be mounted anywhere on the inside of the cap 62a and is preferably welded along the same circumference as the peripheral sensor leads 84a. The small size of the core 60a relative the cap 62a provides a larger annular space between the cap and the core. The annular space is filled with a heat resistant material, such as epoxy resin 90a, thereby further reducing the heat transfer within the tip electrode 36.

The tip-sensor lead 76a and peripheral sensor leads 84a are typically formed of the same material. The sensor lead 76a, 84a, the common lead and the cap 62a material are selected as previously described with reference to FIGS. 3 and 4. In a preferred embodiment, the sensor leads 76a, 84a are formed of constantan, the common lead 42a is formed of alloy-11 and the cap 62a is formed of platinum.

The tip-sensor lead 76a, in combination with the common lead 42a, forms a tip-sensor junction 72a located at or near the apex of the distal end 74a of the active tip electrode 36a. This ensures that the tip-sensor junction 72a is located at or near the electrode/tissue interface when the electrode is oriented in the end-fire mode. Each of the peripheral sensor leads 84a in combination with the common lead 42a forms a peripheral sensor junction 88a located near the outer surface of the cap 62a. A plurality of peripheral sensor junctions 88a combine to form a peripheral thermal sensor system 86a. By increasing the number of peripheral sensor junctions 88a the chances that one of the peripheral sensor junctions is located at or near the electrode/tissue interface when the electrode is oriented in the side-fire mode are increased.

In another configuration, with reference to FIGS. 11a through 12b, a tip electrode 36b in accordance with aspects of the present invention is shown and is adapted to be mounted at the distal end 34 of the electrode device 16. The tip electrode 36b is formed from a solid material core 60b having a plurality of peripheral holes 92b and a center hole 94b bored partially through the core. The core 60b defines the distal-end portion 37 and the proximal-end portion 39 of the tip electrode.

The center hole 94b terminates at a pocket 66b formed approximately in the apex 68b of the domed end 70b of the core 60b. The pocket 66b provides space for mounting the tip-sensor lead 76b and the common lead 42b at or adjacent the distal end 74b of the electrode along the center line. The tip-sensor lead 76b and common lead 42b are soldered within the pocket 66b, at or near the apex 68b, and form a tip-sensor junction 72b. The center hole 94b provides clearance for the tip-sensor lead 76b and common lead 42b allowing the leads to be routed from the tip-sensor junction 72b to the main lumen (not shown) of the catheter.

The peripheral bores 92b are preferably positioned around a circumference of the tubular portion of the core 60b. In a preferred embodiment there are four peripheral bores positioned 90° apart around the circumference of the core. Greater or fewer peripheral bores 92b may be drilled into the core 60b depending on the size of the core and the lead capacity of the catheter lumen. In one embodiment, the peripheral bores 92b are drilled such that a wall of approximately 0.002 inches (0.005 cm) remains between the bore and the outer surface of the core 60b. This spacing ensures that the sensor junctions 88b are located near the surface of the electrode. Within each peripheral bore 92b is a peripheral sensor lead 84b.

The tip-sensor lead 76b and peripheral sensor leads 84b are typically formed of the same material. The sensor lead 76b, 84b, the common lead 42b and the core 60b material are selected as previously described with reference to FIGS. 3 and 4. In a preferred embodiment, the sensor leads 76b, 84b are formed of constantan, the common lead 42b is formed of alloy-11 and the core 60b is formed of platinum.

The tip-sensor lead 76b, in combination with the common lead 42b, forms a tip-sensor junction 72b located at or near the apex of the distal end 74b of the active tip electrode 36b. This ensures that the tip-sensor junction 72b is located at or near the electrode/tissue interface when the electrode is oriented in the end-fire mode. Each of the peripheral sensor leads 84b in combination with the common lead 42b forms a peripheral sensor junctions 88b located near the exterior surface of the core 60b. A plurality of peripheral sensor junctions 88b combine to form a peripheral thermal sensor system 86b. By increasing the number of peripheral sensor junctions 88b the chances that one of the peripheral sensor junctions is located at or near the electrode/tissue interface when the electrode is oriented in the side-fire mode are increased.

Figure 13A:
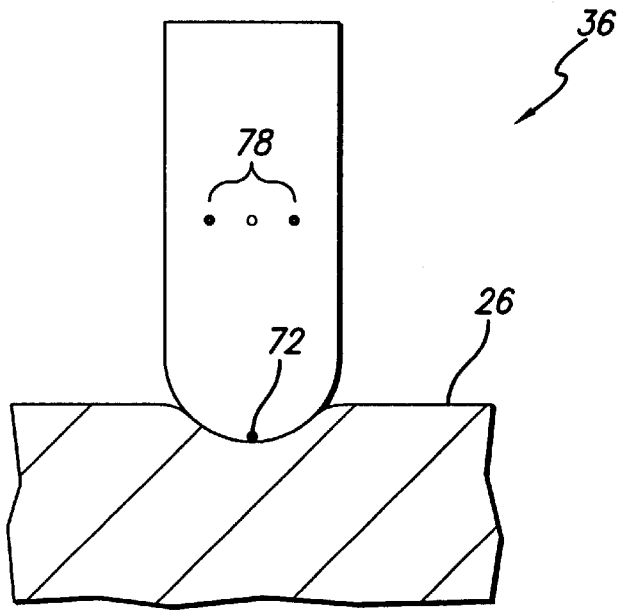
FIG. 13a is a side view of the tip electrode of FIG. 5a operating on a biological site in an end-fire mode.

In operation, the tip electrode 36 is positioned in contact with the target tissue 26 which is located in a biological structure such as the heart, for example, in which fluid, such as blood, flows past the tissue to be ablated. The tip electrode 36 may contact the tissue 26 in several ways. In the end-fire mode, as depicted in FIG. 13a, the tip-sensor junction 72, located at or very near the apex of the electrode, is nearest the tissue 26 while the side sensor junctions 44, 46 are nearer the blood pool. Because the side sensor junctions 44, 46 are within the blood pool they experience a cooling effect. Accordingly, the temperature reading provided by the side sensors 44, 46 is usually less than the temperature reading provided by the tip-sensor junction 72. Experimentation using a conductive fluid that stimulates blood has shown that the temperature difference between the tip-sensor junction 72 at the electrode/tissue interface and the side sensor junctions 44, 46 in the conductive fluid pool is approximately 10° C.

Figure 13B:
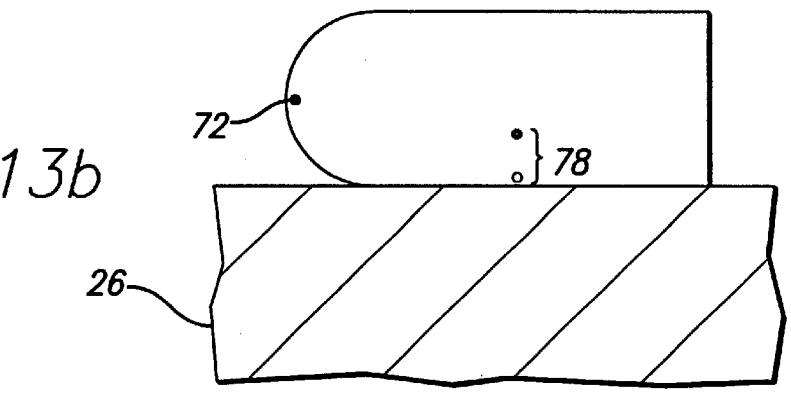
FIG. 13b is a side view of the tip electrode of FIG. 5a operating on a biological site in a side-fire mode.
Figure 13C:
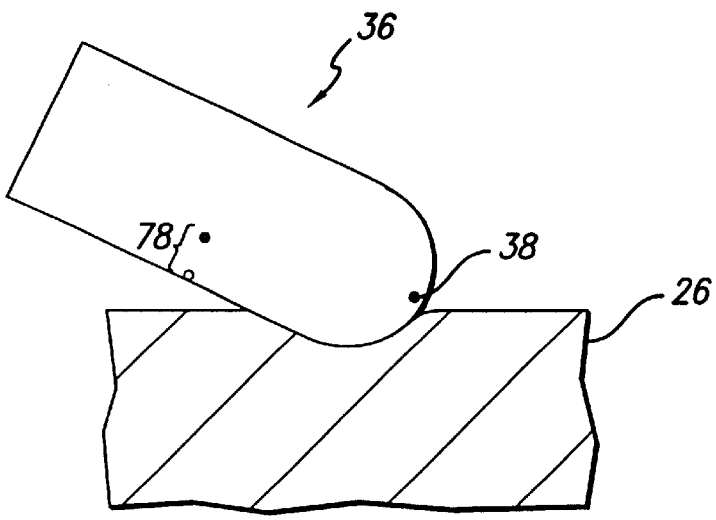
FIG. 13c is a side view of the tip electrode of FIG. 5a operating on a biological site in a mode between the end-fire and side-fire modes.

In the side-fire mode, as depicted in FIG. 13b, at least one of the side sensor junctions 44, 46, located at or very near the cylindrical surface of the electrode along the side of the electrode, contacts the tissue 26 while the tip-sensor junction 72 is within the blood pool. Because the tip-sensor junction 72 is within the blood pool it experiences a cooling effect. Accordingly, the temperature reading provided by the tip sensor 72 is usually less than the temperature reading provided by the side sensor junctions 44, 46. Experimentation using a conductive fluid that simulates blood has shown that the temperature difference between the side sensor junctions 44, 46 at the electrode/tissue interface and the tip-sensor junction 72 in the conductive fluid pool is approximately 10° C.

When the catheter tip is oriented between the pure end-fire and side-fire modes; i.e. between substantially perpendicular and substantially parallel to the tissue 26 surface, as depicted in FIG. 10, neither the tip-sensor junction 72 nor any of the one or more side sensor junctions 44, 46 may contact the tissue. In such situations, the temperature at the electrode/tissue interface is not directly obtainable. Instead, the greatest of the temperatures provided by the tip-sensor junction 72 and the side sensor junctions 44, 46 is used to provide the electrode/tissue interface temperature.

The controller 20 (FIG. 1) monitors the temperatures provided by each of the sensor junctions 44, 46, 72 and adjusts the power provided by the power generator 18 accordingly, in order to prevent the temperature at the electrode/tissue interface from exceeding a predetermined threshold level. The controller 20 reports the temperature measurements for each sensor junction 44, 46, 72, and determines which of the sensor junctions 44, 46, 72 is measuring the highest temperature and compares that measured temperature to the threshold level. If the highest measured temperature is above the threshold temperature, the controller provides control signals to the power generator 18 to reduce the power supplied to the electrode.

It should also be appreciated that the invention can also be applied to other types of ablation catheters employing alternate sources of electrical energy for ablation, such as ultrasound or microwave energy. The invention may also be applied to ablation catheters employing a cryogenic cooling source.

It will be apparent from the foregoing that while particular embodiments of the invention have been illustrated and described, various modifications can be made without departing from the spirit and scope of the invention. Accordingly, it is not intended that the invention be limited, except as by the appended claims.

What is claimed is:

1. A method of determining the orientation of a tip electrode positioned within a biological site having fluid flowing therethrough, the tip electrode carried by a catheter and having a dome shaped distal-end portion with a thermal sensor electrically connected near the apex of the dome and a cylindrical proximal-end portion with at least one thermal sensor electrically connected near the periphery of the proximal-end portion, said method comprising:

measuring the temperature near the apex of the dome;

measuring the temperature near the surface of the periphery of the proximal-end portion; and comparing the apex temperature and the periphery temperature to assess whether the tip electrode is oriented in an end-fire mode, side-fire mode or between the end-fire and side-fire modes.

2. The method of claim 1 wherein the tip electrode comprises a plurality of periphery thermal sensors and measuring the temperature near the surface of the periphery of the proximal-end portion comprises:

measuring the temperature at each periphery thermal sensor; and selecting the highest measured temperature as the periphery temperature.

3. The method of claim 1 wherein the tip electrode is in the end-fire mode when the apex temperature is greater than the periphery temperature by an determined amount.

4. The method of claim 3 wherein the determined amount is approximately 10° C.

5. The method of claim 1 wherein the tip electrode is in the side-fire mode when the periphery temperature is greater than the apex temperature by a determined amount.

6. The method of claim 5 wherein the determined amount is approximately 10° C.

7. The method of claim 1 wherein the tip electrode is between the end-fire and side-fire modes when the periphery temperature is substantially the same as the apex temperature.

8. The method of claim 1 further comprising:

comparing the greater of the apex temperature and the periphery temperature to a threshold value; and adjusting power to the electrode when the greater temperature exceeds a predetermined threshold value.

\* \* \* \* \*

UNITED STATES PATENT AND TRADEMARK OFFICE
CERTIFICATE OF CORRECTION

PATENT NO. : 6,616,657 B2
DATED : September 9, 2003
INVENTOR(S) : John A. Simpson et al.

It is certified that error appears in the above-identified patent and that said Letters Patent is hereby corrected as shown below:

<u>Title page,</u>
Item [56], U.S. PATENT DOCUMENTS, change
 "5,277,201     1/1984  Stern", to read,
-- 5,277,201     1/1994  Stern --.

Signed and Sealed this

Twenty-third Day of March, 2004

JON W. DUDAS
*Acting Director of the United States Patent and Trademark Office*